United States Patent [19]

Ahr

[11] Patent Number: 5,733,273
[45] Date of Patent: Mar. 31, 1998

[54] ABSORBENT MEMBER WITH HIGH DENSITY ABSORBENT WICKING STRIPS

[75] Inventor: Nicholas Albert Ahr, Cincinnati, Ohio

[73] Assignee: The Procter & Gamble Company, Cincinnati, Ohio

[21] Appl. No.: 599,864

[22] Filed: Feb. 13, 1996

Related U.S. Application Data

[63] Continuation of Ser. No. 263,285, Jun. 21, 1994, abandoned.

[51] Int. Cl.$^6$ ........................................ A61F 13/15
[52] U.S. Cl. ................... 604/378; 604/358; 604/384; 604/385.1; 604/368
[58] Field of Search ........................... 604/358, 365, 604/367, 369, 378, 384, 385.1

[56] References Cited

U.S. PATENT DOCUMENTS

| | | | |
|---|---|---|---|
| 700,940 | 5/1902 | Johnson | 604/375 |
| 2,548,341 | 4/1951 | Bricmont | 604/378 |
| 3,095,878 | 7/1963 | Bassett | 604/378 |
| 3,525,338 | 8/1970 | Bernardin | 604/378 |
| 4,082,886 | 4/1978 | Butterworth et al. | 428/284 |
| 4,129,132 | 12/1978 | Butterworth et al. | 128/287 |
| 4,287,251 | 9/1981 | King et al. | 604/369 |
| 4,327,728 | 5/1982 | Elias | 128/285 |
| 4,341,215 | 7/1982 | Eldridge | 128/285 |
| 4,425,126 | 1/1984 | Butterworth et al. | 604/367 |
| 4,573,987 | 3/1986 | Lamb, Jr. | 604/378 |
| 4,596,567 | 6/1986 | Iskra | 604/368 |
| 4,636,209 | 1/1987 | Lassen | 604/378 |
| 4,676,784 | 6/1987 | Erdman et al. | 604/368 |
| 4,699,619 | 10/1987 | Bernardin | 604/378 |
| 4,718,899 | 1/1988 | Itoh et al. | 604/368 |
| 4,755,178 | 7/1988 | Insley et al. | 604/367 |
| 5,021,050 | 6/1991 | Iskra | 604/379 |
| 5,037,412 | 8/1991 | Tanzer et al. | 604/359 |
| 5,122,407 | 6/1992 | Yeo et al. | 428/138 |
| 5,171,391 | 12/1992 | Chmielewski et al. | 604/367 |
| 5,175,046 | 12/1992 | Nguyen | 604/358 |
| 5,364,382 | 11/1994 | Latimer | 604/378 |

FOREIGN PATENT DOCUMENTS

| | | | |
|---|---|---|---|
| 615 736 | 9/1994 | European Pat. Off. | |
| 1028003 | 7/1984 | Japan | 604/385.1 |

OTHER PUBLICATIONS

Kimberly Clark Kotex Maxi sanitary napkins (2, one whole and one dissected).
Kimberly Clark New Freedom sanitary napkins (2, one whole and one dissected).
Personal Products Stayfree Prima sanitary napkins (2, one whole and one dissected).

*Primary Examiner*—John G. Weiss
*Assistant Examiner*—Dennis Ruhl
*Attorney, Agent, or Firm*—Marshall, O'Toole, Gerstein, Murray & Borun

[57] ABSTRACT

According to the present invention, an absorbent member for use in an absorbent core is provided which efficiently acquires and distributes body fluid throughout its entire structure and which maintains open acquisition area for repeated insults of body fluid. The absorbent member comprises an absorbent medium including a low density fibrous material and higher density absorbent strips distributed throughout the absorbent medium. The absorbent strips may be randomly distributed or distributed in a pattern and can be comprised of any paper, tissue or nonwoven or a laminate of paper and superabsorbents. Further, the present invention relates to absorbent articles, such as diapers, sanitary napkins, and adult incontinent pads, comprised of the absorbent members of the present invention.

16 Claims, 3 Drawing Sheets

ABSORBENT MEMBER WITH HIGH DENSITY ABSORBENT WICKING STRIPS

This is a file wrapper continuation of U.S. application Ser. No. 08/263,285, filed Jun. 21, 1994, now abandoned.

FIELD OF THE INVENTION

This invention relates to absorbent structures useful for absorbing body exudates. This invention also relates to absorbent articles, such as diapers and sanitary napkins, for which the absorbent structures are particularly useful.

BACKGROUND OF THE INVENTION

Absorbent articles such as disposable diapers, adult incontinence pads, sanitary napkins and the like are generally provided with absorbent members to receive and retain body liquids. Such absorbent members frequently comprise fibrous web structures which made up of entangled masses of fibers. In order for such absorbent articles to function efficiently, the absorbent members must quickly acquire body liquids into the structure from the point of application and subsequently distribute the body liquids within and throughout the absorbent member to provide maximum liquid containment.

Prior attempts to distribute the liquid within and throughout the absorbent member have frequently utilized continuous fibrous wicking layers or wicking zones within the absorbent member, having a higher density than the remainder of the absorbent member. These layers tend to wick fluid only in the one wicking layer and do not fully distribute the liquid throughout the entire length, width and thickness of the absorbent member. These prior attempts also did not always adequately prevent the lower density area from collapsing upon itself thus destroying the void space of the lower density area and resulting in low fluid acquisition rates and poor containment. The acquisition rates of absorbent members utilizing these layers or zones are also limited by the limited interface area between the high and low density zones.

Thus, it would be advantageous to provide an absorbent member that fully distributes liquid within itself, that maintains open acquisition area for repeated insults of body exudate and that provides increased interface area between high and low density regions within the absorbent member.

SUMMARY OF THE INVENTION

The present invention is directed to improvements in absorbent cores of absorbent articles such as diapers, sanitary napkins and incontinence pads. According to the present invention, an absorbent member for use in an absorbent core is provided which efficiently acquires and distributes body fluid throughout its entire structure and which maintains open acquisition area for repeated insults of body fluid. The absorbent member comprises an absorbent medium including a low density fibrous medium and a plurality of absorbent strips having a higher density than the absorbent medium and which are distributed throughout the absorbent medium. The absorbent strips may be randomly distributed or distributed in a pattern and can be comprised of any paper, tissue or nonwoven or a laminate of paper and superabsorbents. The strips preferably have a width of between about 0.125 inches to about 0.75 inches, a length preferably of between about one inch to about 2.5 inches and a thickness of less than about 0.075 inches.

DETAILED DESCRIPTION OF THE INVENTION

Figure 1:
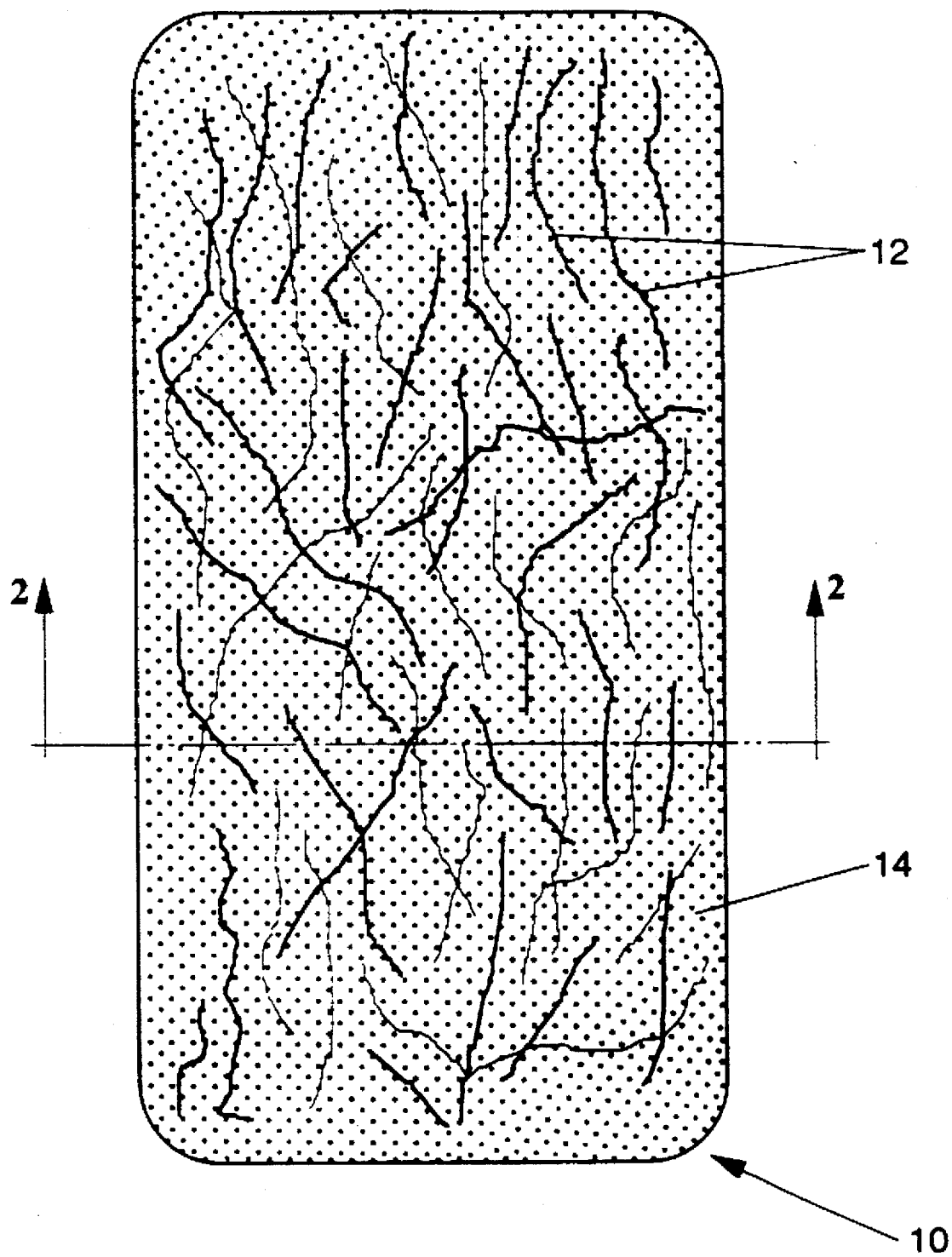
FIG. 1 is a plan view of a preferred absorbent member of the present invention.

The present invention provides improvements for absorbent members for use in absorbent articles such as sanitary napkins, diapers and incontinence pads. These absorbent members are preferably able to both acquire body fluid into an absorbent member and transmit (or wick) the acquired fluid rapidly throughout the absorbent member. Absorbent members of the present invention accomplish both of the these functions by being comprised of a plurality of higher density absorbent strips distributed throughout the length, width and thickness of a lower density absorbent fibrous medium.

The lower density fibrous medium of the present invention has a relatively open fibrous network having a great deal of void space. This open void space allows easy acquisition of body exudate down into the absorbent member or in the z direction. As used herein, the "z direction" refers to the depth or thickness of the absorbent member, the "x direction" refers to the length of the absorbent member and "y direction" refers to the width of the absorbent member. If the open void space is not maintained, the acquisition rate of body exudate is greatly reduced which, as discussed below, can result in failure or leakage.

The absorbent strips of the present invention have a higher density than the absorbent fibrous medium. This density difference creates a capillary gradient difference and a capillary force gradient between the absorbent strips and the fibrous medium. This force gradient tends to rapidly draw already acquired fluid from the fibrous medium into the absorbent strips which then deliver or wick the fluid in the x-y direction to the other portions of the absorbent member. As discussed in greater detail below, this rapid transmission maintains open void space or acquisition area by removing the already acquired fluids from the fibers of the absorbent fibrous medium before the fibers can collapse upon themselves from the weight of the acquired fluid.

As discussed above, to have a capillary gradient necessary for fluid transmission between the fibrous medium and the absorbent strips, the absorbent strips must have a higher density and must usually have a higher basis weight than the absorbent fibrous medium. The density of the absorbent strips can range between about 0.05 g/cm$^3$ to about 0.35 g/cm$^3$, preferably from about 0.10 g/cm$^3$ to about 0.25 g/cm$^3$. The basis weight of the absorbent strips can range between about 0.015 grams per square inch to about 0.25 grams per square inch and preferably from about 0.025 grams per square inch to about 0.15 grams per square inch.

The density of the fibrous medium, which must be lower than the absorbent strips, can range between about 0.025 g/cm$^3$ to about 0.25 g/cm$^3$, or preferably between about 0.050 g/cm$^3$ to 0.15 g/cm$^3$. The basis weight of the fibrous medium is generally between about 0.05 grams per square inch to about 0.25 grams per square inch.

The density of the absorbent member comprised of the lower density fibrous medium and the higher density wicking strips can range between about 0.05 g/cm$^3$ to about 0.25 g/cm$^3$. When it is impractical to measure the density of the fibrous medium portion of the composite absorbent member, measuring the density of the absorbent member as a whole will suffice. If the density of the absorbent member is lower than the density of the wicking strips, the density of the fibrous medium must also be lower than the density of the wicking strips. Density of the absorbent member at any given location is determined by measuring the basis weight of the absorbent member at that location and dividing by the thickness of the absorbent member.

For example, a given area or a portion of the absorbent member may be cut from the absorbent member and weighed to determine its basis weight and then divided by its thickness to determine the absorbent member density at that location. The density of the absorbent member at that location should be less than the density of any absorbent strip found in that portion of the absorbent member.

The thickness of the absorbent strips, and the thickness of the absorbent member and the absorbent fibrous medium needed to determine densities are determined by using any conventional gauge with a confining pressure of 32 grams per 0.78 square inches. An especially useful caliper gauge is the "Linear Gauge Sensor" model No. 65503 made by ONO SOKKI of Japan having a one inch diameter circular foot.

Since, the absorbent strips are distributed throughout the x, y and z directions within the absorbent fibrous mediums the absorbent mender can efficiently distribute fluid throughout its entire depth width and length. For maximum fluid distribution throughout the entire absorbent member, it is preferred that a portion of each absorbent strip touch at least a portion of another absorbent strip. This contact allows the transfer of fluid from one absorbent strip to another which enables fluid to be wicked throughout the entire absorbent member. If there was no contact, wicking of fluid would slow down greatly as the lower density fibrous medium would not have the capillary force necessary to draw the fluid out of the absorbent strip and deliver it to another absorbent strip or another portion of the absorbent member. This contact is most important for wicking in the x direction, or length of the absorbent member, as this is the furthest distance the fluid must travel.

The ability to quickly transmit acquired fluid from low density areas to high density areas is partially dependent on the interface area between these two different density areas. The present invention provides methods for increasing the interface area between the low density and high density areas of the absorbent member.

Though some contact or overlap is preferred between the absorbent strips for fluid transmission, it is preferred that this contact be kept to a reasonable minimum. This minimum absorbent strip contact or overlap allows the maximum surface area of the absorbent strips to be exposed to and in contact with the fibrous absorbent medium, as most of the surface area of the absorbent strips is in contact with the fibrous medium rather than covered and in contact with other absorbent strips. Due to the capillary gradient between the fibrous medium and the absorbent strips, this maximum absorbent strip surface area contact or interface provides rapid transmission of acquired fluid to the absorbent strips from the fibrous medium surrounding all four nearly completely exposed (top, bottom, and side) surfaces of the absorbent strips. In addition, this rapid transmission is enhanced since a plurality of absorbent strips are distributed throughout the fibrous medium. Acquired fluid in a given area of the fibrous medium would be drained by several, rather than one, of these absorbent strips in that area. This rapid transmission helps maintain open acquisition area and prevents the fibrous medium (or capillary walls) from having time to collapse upon itself due to the weight of the absorbed body fluid. If the capillaries collapse, fluid which would normally be conducted downward into the absorbent member would tend to remain at or near the top surface of the absorbent member. If the absorbent member comprises the absorbent core of an absorbent article, as discussed below, this fluid at the surface may either rewet or fail to penetrate an absorbent article topsheet thereby producing a wet uncomfortable absorbent article surface. Thus leakage containment characteristics are improved by more quickly acquiring and distributing liquid into and throughout the absorbent member.

The low density fibrous medium of the present invention can be comprised of a variety of fibrous materials including wood pulp, treated wood pulp, and synthetic fibers or mixtures thereof. These fibers can be staple length fibers having a length of between about 0.125 inches to about 3 inches. A portion of or the entire fibrous medium can be comprised of treated or synthetic fibers. These fibers aid in maintaining open acquisition area and preventing capillary collapse, because they are stiff and resilient and resist collapse. Such fibers include polyester, polypropylene, nylon or copolymers of the above. These fibers also include modified cellulose fibers such as disclosed in U.S. Pat. No. 5,183,707 which issued Feb. 2, 1993 to Herron et. al. and which is incorporated herein by reference.

The lower density fibrous medium can also include superabsorbents to enhance total absorbency.

The higher density absorbent strips of the present invention can be comprised of almost any material, including nonwovens, tissue or paper which can each further have wet and dry strength resins and a basis weight of between about 0.010 grams per square inch to about 0.30 grams per square inch, preferably between about 0.03 grams per square inch to about 0.10 grams per square inch.

The absorbent strips can also contain value added particles for absorbency or other purposes. These materials include fibrous or granular superabsorbents (sometimes referred to as hydrogel-forming polymers), odor control materials or desiccants. To entrap these value added materials, the absorbent strips can optionally have a laminar construction. For example, the absorbent strip can preferably be a tissue laminate comprised of a top tissue layer, a bottom tissue layer, and value added particles disposed between the two tissue layers, and an adhesive that connects the two tissue layers together and maintains the superabsorbent between the tissue layers.

The laminate tissue layers may be an airlaid or wetlaid structure comprised of natural fibers, modified wood fibers, synthetic fibers or any combination of these materials. The synthetic fibers can be polypropylene, polyethylene, rayon or nylon. They can also be single component or bi-component fibers which can be temperature stable or thermal bondable. Thirty seven pound per 3000 square feet airlaid tissue manufactured by Ft. Howard or twenty seven pound per 3000 square feet wetlaid tissue manufactured by Procter & Gamble Co. (and sold in a 2-ply product as Bounty® paper towels) have been found to be very useful.

The laminate adhesive may be comprised of a pressure sensitive, a non-pressure sensitive, a latex type or any other type adhesive known to the art. The adhesive also can contain elastomeric elements if desired. Adhesive type 2158 manufactured by Findley Adhesives, Inc. of Wauwatosa, Wis. has been found very useful.

The superabsorbent materials entrapped in the laminate are comprised of substantially water-insoluble inorganic or organic compounds capable of absorbing ten times or more of their own weight in fluids and retaining these fluids under pressure. The superabsorbents can be in the form of fibers, spheres, particle, bits of film or webs. Superabsorbents, or hydrogel-forming polymers, as disclosed in U.S. Pat. Reissue No. 32,649 to Brandt et al., and incorporated herein by reference, are useful superabsorbents. Nalco 1180 also has been found to be a suitable superabsorbent. The value added particles can comprise up to about 99 percent by weight of the absorbent strips, preferably less than 67 percent by weight and most preferably 33–50 percent by weight.

Absorbent strips useful in practicing the invention have a variety of dimensions. The strips have a length to width ratio of at least about 4:1 and preferably at least about 10:1. The absorbent strips can have a length from between about 0.50 inches up to about the length of the absorbent member. Preferably, the length ranges between about 1 inch to a length less than the width of the absorbent member usually less than about 2.5 inches in the case of sanitary napkins. The width of the strips can be between about 0.10 inches to about 1.50 inches, preferably about 0.125 inches to about 0.75 inch and most preferably about 0.25 inches. The thickness of the strips can be between about 0.001 to about 0.125 inches. The individual absorbent strips can all have the same dimensions or their dimensions can vary throughout the absorbent member.

The absorbent strips can comprise between about 5 to about 75 percent by weight preferably less than 50 percent by weight of the absorbent member and can be distributed in a variety of ways within the absorbent member. For optimum fluid distribution, it is preferred that the absorbent strips are distributed to cover the majority of the length (x direction) and width (y direction) of the absorbent member. To fully distribute the acquired fluid throughout the absorbent member, it is preferred that at least fifty percent of the x/y projected plane area be covered by absorbent strips. The "x/y projected plane" includes all the x/y planes throughout the depth of the absorbent member. A point on the x/y projected plane area is considered covered if any point along a line normal to the top x/y surface of the absorbent member comes in contact with an absorbent strip.

In addition to having x/y direction absorbent strip coverage, it is also preferred that a majority of the absorbent strips each be within an absorbent strip width ("w") distance of another absorbent strip in the x/y projected plane area. If the width of two absorbent strips differ, w equals the width of the narrower strip. A first absorbent strip is within an absorbent strip width of another absorbent strip in the x/y projected plane area, if along any x/y plane a perpendicular line is extended in the z direction that is not greater than a distance of w away from any edge of the first absorbent strip and comes in contact with another absorbent strip. This placement of the absorbent strips allows fluid to be quickly acquired and dispersed throughout the entire absorbent member.

The absorbent strips are not only distributed throughout the width and length of the absorbent member but are also distributed throughout the thickness of the absorbent member as well. It is preferred, however, that a layer in the z direction closest to the body-facing surface (i.e. the surface that will first encounter body fluid) of the absorbent member contain no absorbent strips, but only the lower density fibrous absorbent medium. This layer is sometimes referred to as a dusting layer. Having no absorbent strips at the body surface of the absorbent member allows body fluid to be easily acquired into a depth of the absorbent member before it contacts any of the higher density absorbent strips. This prevents the possibility of body fluid staying at or near the surface of the absorbent article while it is waiting to be acquired by the absorbent member. For instance, if body fluid was deposited directly over a higher density absorbent strip with little void space, the fluid would take longer to be acquired than if deposited over the lower density fibrous medium which has a larger amount of void space. If the absorbent member makes up the absorbent core of an absorbent article, this slower acquisition may cause deposited body fluid to remain on the topsheet of an absorbent article or cause the topsheet to be rewet from the fluid on the body surface of the absorbent member. Either situation causes discomfort to the wearer.

As discussed in further detail below and as seen in the figures, the absorbent strips can be randomly distributed, homogeneously distributed or distributed in predetermined patterns throughout the x, y and z directions.

Figure 2:
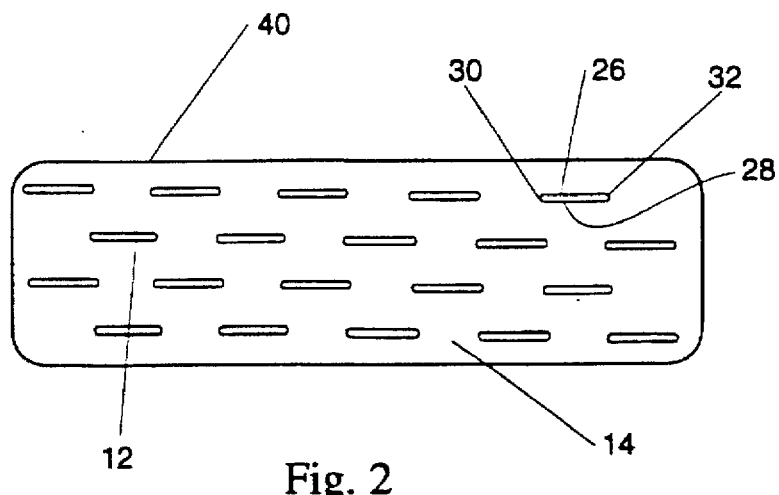
FIG. 2 is a schematic cross-sectional view taken generally along line 2—2 of FIG. 1.

FIGS. 1–5 show various embodiments of the present invention. As seen in FIGS. 1 and 2, an absorbent member 10 of the present invention is provided comprising a plurality of absorbent strips 12 randomly distributed throughout an absorbent fibrous medium 14. The absorbent strips 12 are distributed throughout the entire x, y, z directions of the absorbent member 10.

Figure 3:
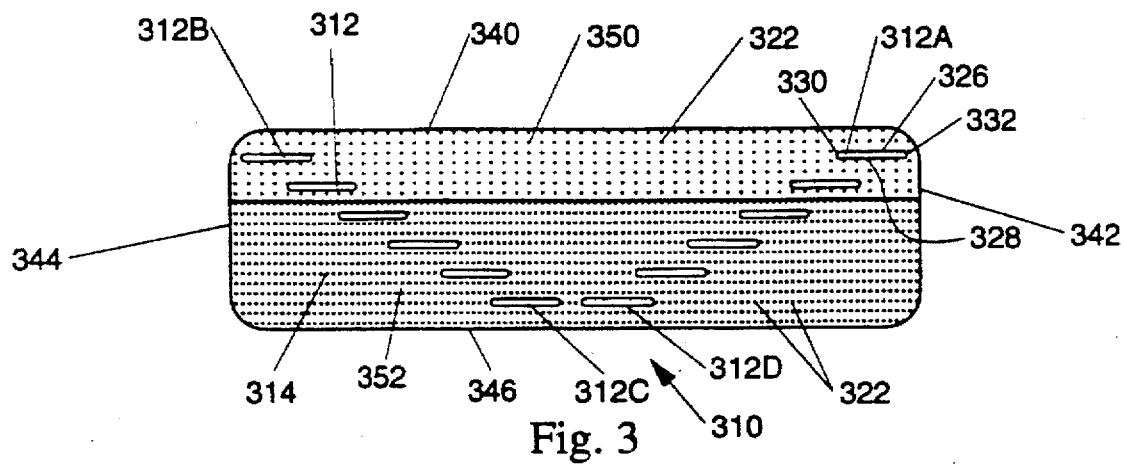
FIG. 3 is a schematic cross-sectional view of a further embodiment of the absorbent member of the present invention.

In addition to the homogenous random placement of the absorbent strips 12 in the absorbent member 10, as shown in FIGS. 1–2, the absorbent strips may also be arranged in a predetermined pattern within the absorbent member. As seen in FIG. 3, an alternative absorbent member 310 of the present invention is provided which includes absorbent strips 312 distributed in a fibrous medium 314 in a predetermined "V" pattern. As seen in FIG. 3, the absorbent strips 312A and 312B closest to the top or body facing surface 340 of the absorbent member 310 are closest to the longitudinal edges 342 and 344 of the absorbent member 310. Progressing down away from the top surface 340 to the bottom surface 346 the absorbent strips 312 are located closer to the center of the width of the absorbent member 310 and further away from the longitudinal edges 342 and 344 of the absorbent member 310. This pattern provides a large acquisition zone for insults from heavy fluid flow users. The fluid easily enters into the low density fibrous medium 314 above the higher density absorbent 312 strips and quickly flows to the bottom of the absorbent member 310 under capillary control contacting some of the absorbent strips 312 on the way down through the pad. At this point it comes into contact with other absorbent strips 312C and 312D near the center of the bottom surface of the absorbent member 310 which continue to drain the low density fibrous medium 314 making room for the next fluid insult. This pattern also provides wicking and storage along the sides of the absorbent member to prevent side leakage due to fluid flowing over the sides.

Figure 4:
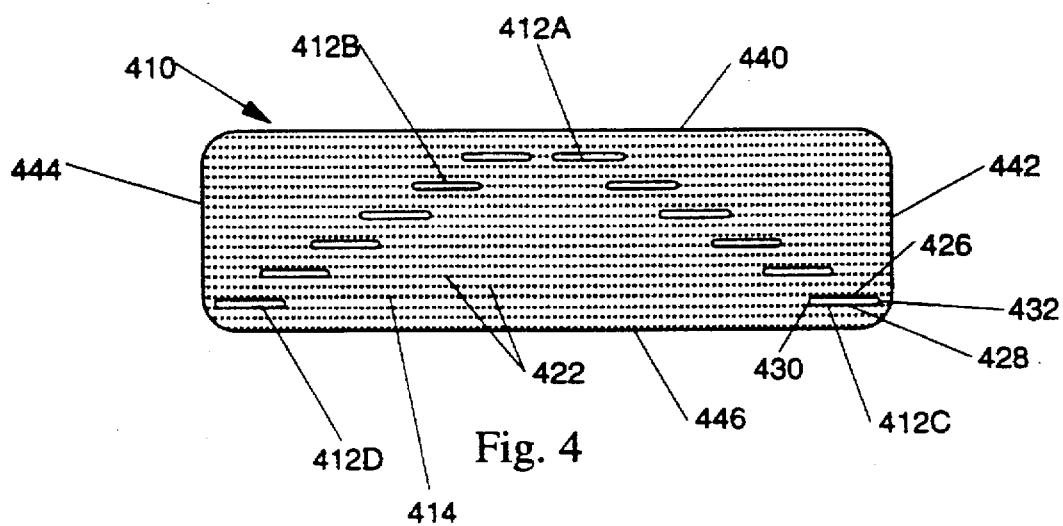
FIG. 4 is a schematic cross-sectional view of a third embodiment of the absorbent member of the present invention.

As seen in FIG. 4, another alternative embodiment of the present invention is provided. An absorbent member 410 is provided where the absorbent strips 412 are distributed in an absorbent fibrous medium 414 in an inverted V pattern. As seen in FIG. 4, the absorbent strips 412A and 412B closest to the top surface 440 of the absorbent member 410 are closest to the center of the width of the absorbent member 410 and furthest away from the longitudinal sides 442 and 444 of the absorbent member 410. As one moves from the top or body-facing surface 440 to the bottom surface 446 of the absorbent member 410, the absorbent strips are placed closer to the longitudinal edges 442 and 444 of the absorbent member 410. The absorbent strips 412C and 412D closest to the bottom surface 446 are also closest to the longitudinal edges 442 and 444. This pattern is designed to provide continued wicking of medium to light fluid insults and an occasional heavy fluid insult. The medium to light fluid insult enters the core through the low density fibrous medium closest to the absorbent strips 412A and 412B which quickly drain the fibrous medium to keep the absorbent member ready for the next insult. If a heavy fluid insult occurs, the fluid that does not have the time to be drained by strips 412A and 412B will cascade down through another portion of the low density fibrous medium 414 and over another or several more absorbent strips which will drain the fibrous medium 414.

Also, as seen in FIGS. 2–4, the top 26, 326, 426, bottom 28, 328, 428 and side 30, 32, 330, 332, 430, 432 surfaces of the absorbent strips 12, 312, 412 are all exposed to the low density fibrous medium 14, 314, 414. As discussed above this maximum surface area exposure allows rapid transmission of acquired fluid from the fibrous medium 14, 314, 414 on all four sides of the absorbent strips 12, 312, 412 which maintain open acquisition area.

As discussed above, the absorbent strips can contain superabsorbents. Both the amount and type of superabsorbent can vary between strips. It is preferred that individual strips only contain one type of superabsorbent. If different types of superabsorbents are used between strips, it is preferred that this change vary between strips in the z direction. It is preferred that the strips closest to the body facing surface contain superabsorbents that absorb and swell slowly and that the strips furthest from the body-facing surface have fast absorbency rates. It is believed that this type of z gradient superabsorbent variation will allow a fluid to rapidly be acquired into the thickness of the absorbent members and prevent the area near the body-facing surface from remaining wet. For example, it is preferred that the absorbent strips located in upper half of the z direction thickness contain superabsorbents that are able to absorb exudate at such a rate that they reach at least about 80% of their capacity no faster than 120 seconds such as the superabsorbent sold under Nalco 1180 brand name. It is also preferred that the absorbent strips in the bottom half of the z direction thickness contain superabsorbents that absorb exudates at such a rate that they reach at least 80% of their capacity in less than 60 seconds, preferably less than 45 seconds, such as superabsorbents sold under the Fibersorb SA7200 brand name (formerly manufactured by Arco Chemical Co. of Newton Square, Pa.). A suitable method for the percent rate of capacity is described in allowed U.S. patent application Ser. No. 07/637,090 filed by Noel, et al. on Jan. 3, 1991 (PCT international Publication No. WO 92/11830) published on Jul. 23, 1992, which is incorporated herein by reference.

For the same reasons, if the amount of superabsorbent varies betweens strips, it should vary in the z direction with strips containing the lowest loading of superabsorbents near the body facing surface and strips containing the highest loading of superabsorbency furthest away from the body facing surface. If the amount of superabsorbent varies between strips, it is preferred that the strips in the top half of the z direction thickness between the body facing surface and the middle of the thickness of the absorbent member, contain between about 0–50 percent by weight of the total superabsorbent contained in all the absorbent strips of the absorbent member and the strips in the lower half of the z direction thickness contain between about 50–100 percent by weight of the total superabsorbent contained in all the strips.

As shown in FIGS. 2–4 and discussed above, the absorbent fibrous medium 214, 314, and 414 may not contain superabsorbents or may contain superabsorbents in various distributions. As seen in FIG. 2, the absorbent fibrous medium 214 contains no superabsorbent particles. As seen in FIG. 4, superabsorbent particles 422 are distributed in a near uniform distribution throughout the thickness of the absorbent member 410. While, as seen in FIG. 3, a top layer 350 of the absorbent member 310 has a low loading of superabsorbent particles 322 in the fibrous medium 314 and a bottom layer 352 has a heavier or more dense loading of superabsorbent particles 322. The basis weight of the superabsorbents in the top layer 350 can range between about 0.01 grams per square inch to about 0.035 grams per square inch. The basis weight of the superabsorbents in the bottom layer 352 can range between about 0.02 grams per square inch to about 0.070 grams per square inch.

Figure 5:
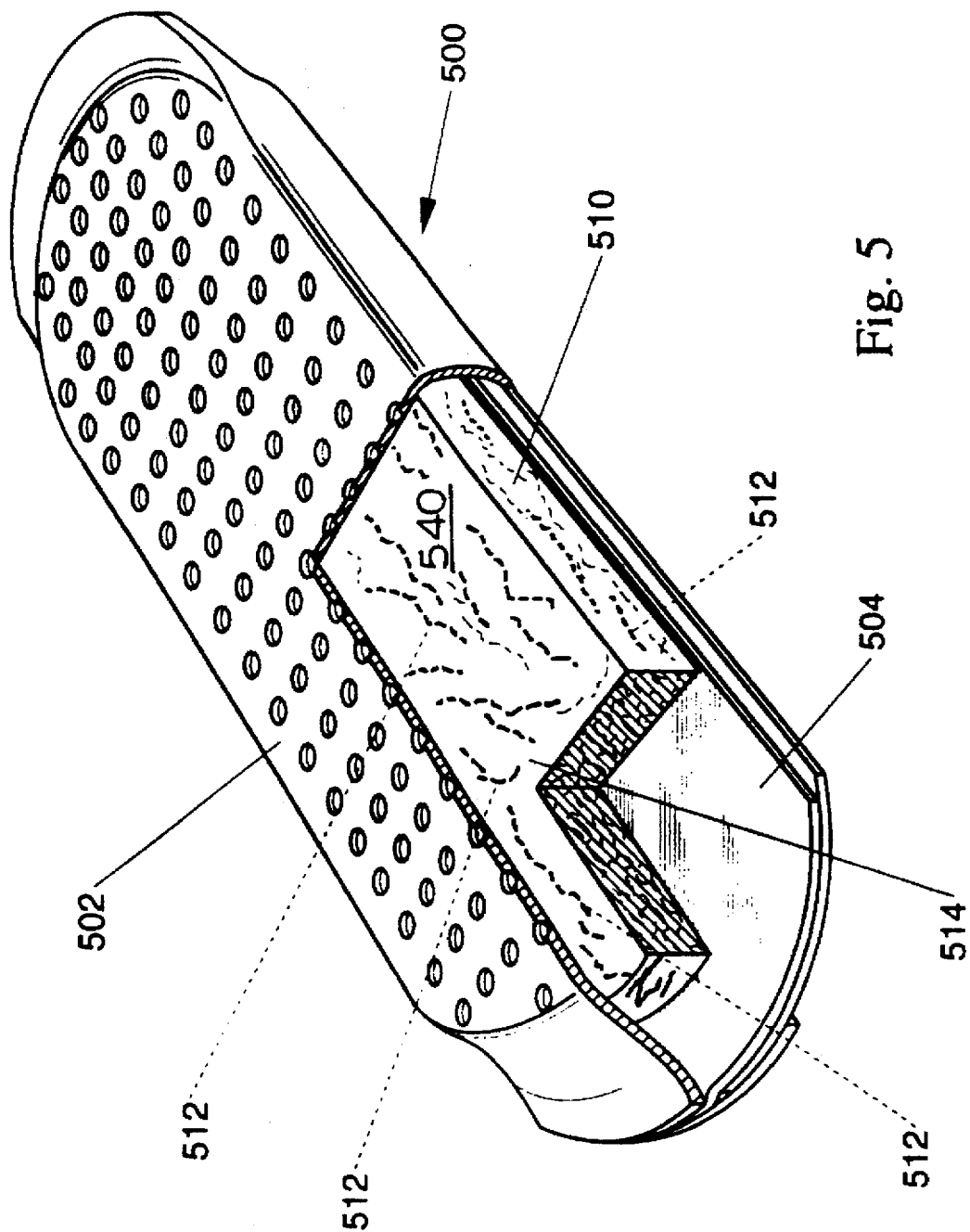
FIG. 5 is a perspective plan view partially in cross section of a disposable absorbent article utilizing one embodiment of the present invention.

As seen in FIG. 5, an absorbent article 500, a sanitary napkin, which utilizes the absorbent members of the present invention is provided. The absorbent article 500 contains a liquid pervious topsheet 502 joined to a liquid impervious backsheet 504. Disposed between the topsheet 502 and backsheet 504 is an absorbent member 510 of the present invention. As seen in FIG. 5, the absorbent member 510 has absorbent strips 512 randomly distributed in an absorbent fibrous medium 514 similar to the distribution shown in FIGS. 1–2.

As seen in FIG. 5 and as also seen in FIGS. 2–4, the layers by the top or body surfaces 540, 440, 340, 40 of the absorbent members 510, 410, 310, 10 contain no absorbent strips but only the lower density fibrous absorbent medium 514, 414, 314, 14. As discussed above, these preferred dusting layers prevent slow fluid acquisition and rewet problems.

The absorbent members of the present invention may also be disposed between fluid pervious topsheets and fluid impervious backsheets of absorbent articles such as diapers and adult incontinent pads.

In addition to providing efficient fluid distribution throughout the absorbent member, the absorbent strips provide the absorbent member with better core integrity than an absorbent member consisting of only wood pulp fluff without absorbent strips. For example, an absorbent member consisting of a fibrous medium of wood pulp fluff with absorbent strips comprised of a laminates having top and bottom tissue layer with superabsorbent there between randomly distributed in the woodpulp had higher tensile strengths than a fluff alone absorbent members.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. An absorbent article comprising a fluid pervious topsheet, a fluid impervious backsheet, and an absorbent core disposed between said topsheet and said backsheet, said absorbent core having a density and comprising:

an absorbent medium comprising a first fibrous network; and a plurality of wicking strips distributed throughout a length, width, and thickness of said absorbent medium, each strip comprising a second fibrous network having a density higher than the density of the absorbent core and comprising a material selected from the group consisting of paper, tissue and nonwoven materials, more than half of said wicking strips being in physical contact with at least one other said wicking strip, and at least 50% of an x/y projected plane area of said absorbent core being covered by said wicking strips, wherein said x/y projected plane is defined by a line oriented in a direction "x" along the length of the absorbent core and a line oriented in a direction "y" along the width of the absorbent core, more than half of said wicking strips being within one wicking strip width of another said wicking strip in said x/y projected plane.

2. An absorbent member for use in an absorbent core, said absorbent member having a density and comprising:

an absorbent medium comprising a first fibrous network; and a plurality of wicking strips distributed throughout a length, width, and thickness of said absorbent medium, each strip comprising a second fibrous network having a density higher than the density of the absorbent member and comprising a material selected from the group consisting of paper, tissue and nonwoven materials, more than half of said wicking strips being in physical contact with at least one other said wicking strip, and at least 50% of an x/y projected plane area being covered by said wicking strips wherein said x/y projected plane is defined by a line oriented in a direction "x" along the length of the absorbent member and a line oriented in a direction "y" along the width of the absorbent member, more than half of said wicking strips being within one wicking strip width of another said wicking strip in said x/y projected plane.

3. An absorbent member, for use in an absorbent core wherein said absorbent member has a density and comprises:

an absorbent medium comprising a first fibrous network; and a plurality of wicking strips distributed throughout a length, width, and thickness of said absorbent medium, each strip comprising a second fibrous network having a density higher than the density of the absorbent member and comprising a material selected from the group consisting of paper, tissue and nonwoven materials, more than half of said wicking strips being in physical contact with at least one other said wicking strip and said strips being present in an amount sufficient to deliver fluid across an x/y projected plane area wherein said x/y projected plane is defined by a line oriented in a direction "x" along the length of the absorbent member and a line oriented in a direction "y" along the width of the absorbent member.

4. The absorbent member of claim 3 wherein said wicking strips comprise up to 50 percent by weight of said absorbent member.

5. The absorbent member of claim 3 wherein said first fibrous network comprises materials selected from the group consisting of wood pulp fiber, synthetic fibers, modified woodpulp fiber and mixtures thereof.

6. The absorbent member of claim 5 wherein said absorbent medium further comprises superabsorbents.

7. The absorbent member of claim 3 wherein each of said wicking strips has a density of from 0.10 $g/cm^3$ to 0.25 $g/cm^3$, inclusive, a length of from 1 inch to 2.5 inches, inclusive, a width of from 0.125 inches to 0.75 inches, inclusive, and a thickness of from 0.001 inches to 0.125 inches, inclusive.

8. The absorbent member of claim 7 wherein each of said wicking strips has a basis weight of from 0.010 grams per square inch to 0.30 grams per square inch, inclusive.

9. The absorbent member of claim 7 wherein said wicking strips comprise paper and superabsorbents, wherein said superabsorbents comprise up to 50 percent by weight of said wicking strips, said wicking strips comprise a laminate of said paper and said superabsorbents.

10. An absorbent article comprising a fluid previous topsheet, a fluid impervious backsheet, and an absorbent core disposed between said topsheet and said backsheet, said absorbent core having a density and comprising:

an absorbent medium comprising a first fibrous network; and a plurality of wicking strips distributed throughout a length, width, and thickness of said absorbent medium, each strip comprising a second fibrous network having a density higher than the density of the absorbent core and comprising a material selected from the group consisting of paper, tissue and nonwoven materials, more than half of said wicking strips being in physical contact with at least one other said wicking strip and said strips being present in an amount sufficient to deliver fluid across an x/y projected plane area wherein said x/y projected plane is defined by a line oriented in a direction "x" along the length of the absorbent core and a line oriented in a direction "y" along the width of the absorbent core.

11. The absorbant article of claim 10 wherein said wicking strips comprise up to 50 percent by weight of said absorbant core.

12. The absorbent article of claim 10 wherein said first fibrous network comprises materials selected from the group consisting of wood pulp fiber, synthetic fibers, modified woodpulp fiber and mixtures thereof.

13. The absorbent article of claim 12 wherein said absorbent medium further comprises superabsorbents.

14. The absorbent article of claim 10 wherein each of said wickingstrips has a density of from 0.10 $g/cm^3$ to 0.25 $g/cm^3$, inclusive, a length of between one inch and 2.5 inches, inclusive, a width of between 0.125 inches and 0.75 inches, inclusive, and a thickness of between 0.001 inches and 0.125 inches, inclusive.

15. The absorbent article of claim 14 wherein said wicking strips each have a basis weight of between 0.010 grams per square inch and 0.30 grams per square inch.

16. The absorbent article of claim 14 wherein said wicking strips comprise paper and superabsorbents, said superabsorbents comprise up to 50 percent by weight of said wicking strips, said wicking strips comprise a laminate of said paper and said superabsorbents.

* * * * *